United States Patent
Kulaev et al.

(10) Patent No.: US 7,150,985 B2
(45) Date of Patent: Dec. 19, 2006

(54) BACTERIOLYTIC COMPLEX, METHOD FOR PRODUCING SAID COMPLEX AND STRAIN FOR CARRYING OUT SAID METHOD

(75) Inventors: Igor Stepanovich Kulaev, Moscow (RU); Olga Andreevna Stepnaja, Puschino (RU); Irina Matveevna Zfasman, Puschino (RU); Taisija Sergeevna Tchermenskaja, Puschino (RU); Larisa Aleksandrovna Ledova, Puschino (RU); Ljudmila Grigorevna Zubrizkaja, Puschino (RU); Vassily Konstantinovich Akimenko, Puschino (RU)

(73) Assignee: Institut Biokhimii I Fisiologii Mikroorganismov IM. G.K.Skrjabina Rossiiskoi Akademii Nauk (IBFM RAN), Puschino (RU)

( * ) Notice: Subject to any disclaimer, the term of this patent is extended or adjusted under 35 U.S.C. 154(b) by 163 days.

(21) Appl. No.: 10/181,498

(22) PCT Filed: Nov. 28, 2001

(86) PCT No.: PCT/RU01/00514

§ 371 (c)(1),
(2), (4) Date: Jul. 18, 2002

(87) PCT Pub. No.: WO02/44352

PCT Pub. Date: Jun. 6, 2002

(65) Prior Publication Data

US 2003/0148497 A1    Aug. 7, 2003

(30) Foreign Application Priority Data

Nov. 29, 2000  (RU) .............................. 2000129650

(51) Int. Cl.
*P12N 1/20* (2006.01)
(52) U.S. Cl. ................... 435/252.1; 435/115; 435/114; 424/94.1; 424/94.6; 424/94.2

(58) Field of Classification Search ................ 435/115, 435/114, 252.1; 424/94.1, 94.6, 94.2
See application file for complete search history.

(56) References Cited

U.S. PATENT DOCUMENTS

| 3,816,260 A | 6/1974 | Sugiyama ..................... 195/62 |
| 3,963,577 A | 6/1976 | Shinkarenko et al. ......... 195/62 |

FOREIGN PATENT DOCUMENTS

| GB | 1353877 | 5/1974 |
| RU | 1549227 | 12/1995 |
| SU | 1755581 | 11/1990 |
| SU | 1774658 | 11/1990 |

OTHER PUBLICATIONS

Stepnaya, O.A., et al "Lysoamidase: A Bacteriolytic Enzyme-Polysaccharide Complex of Microbial Origin . . . Polysaccharide" *Biokhimiya*, vol. 58, No. 10, p. 1523-1528, (1993).
Egorov, N.S. "Bases of the doctrine of antibiotics" *Vysshaya Shkola*, p. 347-349, (1979).
Schindler, C.A., et al. "Lysostaphin: A New Bacteriolytic Agent for the Staphylococcus" *Proc.N.A.S.*, vol. 51, p. 414-421, (1964).
Stepnaya, O.A., et al. "Bacteriolytic enzymes" *Uspekhi biologicheskoy khimii*, vol. XXXIX, p. 341 (1999).
Likhosherstov, L.M., et al. "Structure of an acidic polysaccharide present in the bacteriolytic complex lysoamidase" *FEBS Letters*, vol. 368, p. 113-116, (1995).

*Primary Examiner*—Irene Marx
(74) *Attorney, Agent, or Firm*—Ladas and Parry LLP

(57) ABSTRACT

The inventions relate to the field of medicine, veterinary and biotechnology and may be used for production of a drug for medical and veterinary purposes. A bacteriolytic complex, produced by the bacterium *Lysobacter* sp. XL1, has been proposed, which contains bacteriolytic enzymes (muramidase, muramoylalanineamidase, endopeptidase, a bacteriolytic enzyme with a molecular weight of about 22 kDa), protease, polysaccharide, and ballast components. The method of production of the bacteriolytic complex includes cultivation of the strain-producer on a nutrient medium containing glucose, peptone, yeast extract or yeast autolysate, phosphate salts of sodium and potassium, magnesium sulfate, potassium chloride, iron sulfate, and water.

4 Claims, 1 Drawing Sheet

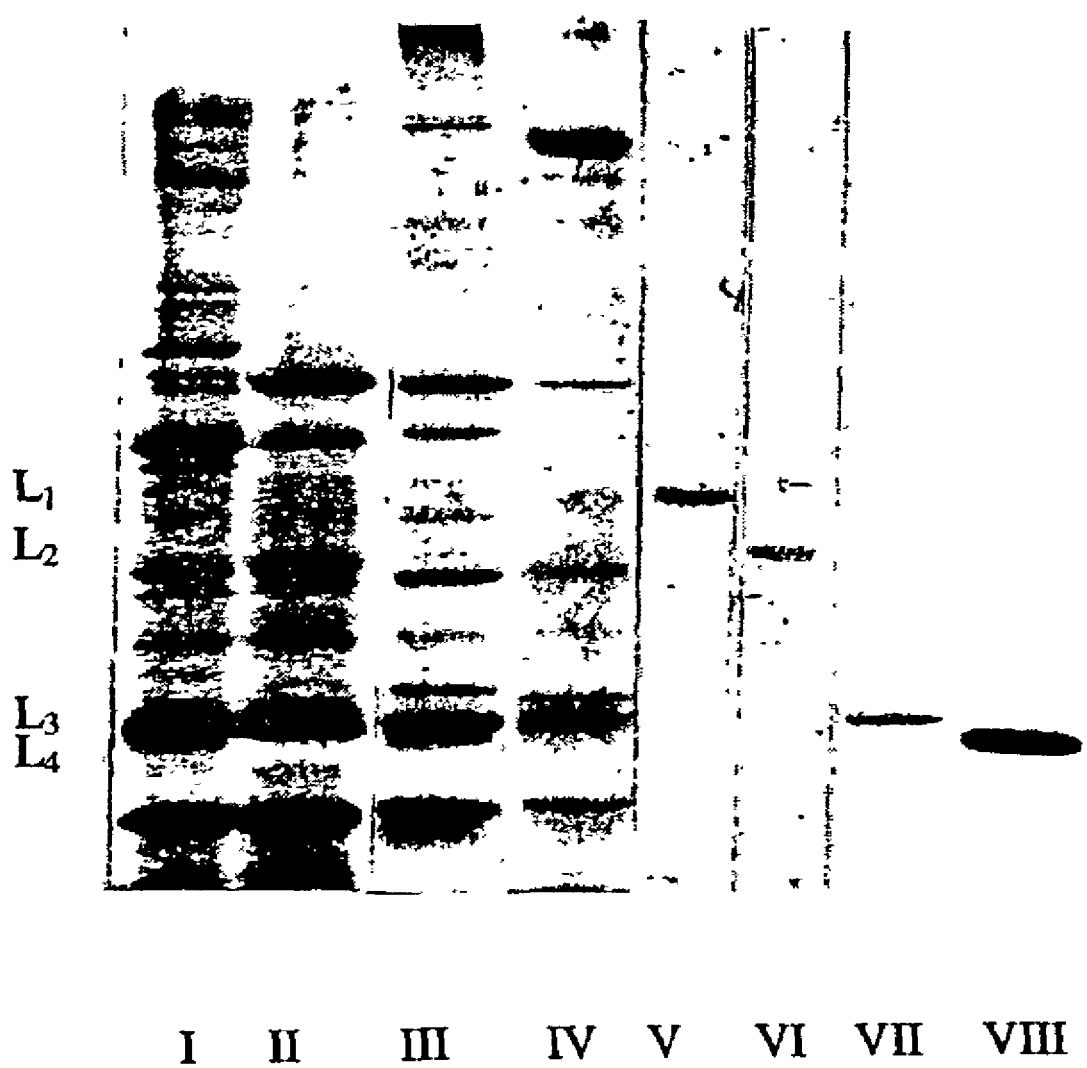

BACTERIOLYTIC COMPLEX, METHOD FOR PRODUCING SAID COMPLEX AND STRAIN FOR CARRYING OUT SAID METHOD

TECHNICAL FIELD

The inventions relate to the field of biotechnology, medicine, and veterinary, more precisely concerning a bacteriolytic complex, and may be used for production of a drug for medicine and veterinary.

BACKGROUND

It is known that bacteriolytic preparations are used as drugs in treatment for a number of diseases caused by pathogenic microflora, including that resistant to antibiotics.

The preparation having bacteriolytic effect—lysozyme is known (Egorov N. S. Bases of the doctrine of antibiotics, 1979, "Vysshaya shkola", p. 347–349). Lysozyme of egg protein is active against a narrow spectrum of microorganisms, limited mainly by micrococci. By specificity of action on microbial cell wall peptidoglycan, lysozyme is a muramidase, i.e., lyzes the bond between muramic acid and glucosamine with the formation of fragments with muramic acid on the reducing end.

That is why lysozyme lyzes the narrow spectrum of gram-positive microorganisms. In particular, it does not lyze cell walls of staphylococci—gram-positive pathogenic bacteria, which are distinguished by the presence of pentaglycine interpeptide bridge that gives additional hardness to their cell wall. Besides, like most enzyme preparations, lyzozyme is not stable enough. All the above concerns also lysozymes from other, e.g., plant or bacterial, sources.

The enzyme preparation is also known, which is based on bacteriolytic enzymes—lysostaphin (Schindler C. A., Schuchardt V. T. Lysostaphin: a new bacteriolytic agent for the *Staphylococcus*. 1964, Proc. of the Nation, Acad. Sci. USA, v. 51, N 3, pp. 415–421).

However, it is unstable and applied in laboratory practice only.

The complex of bacteriolytic enzymes is known, which lyzes gram-positive microorganisms, in particular, pathogenic antibiotic-resistant staphylococci and other microorganisms, and which is obtained from culture liquid of bacterium *Xanthomonas campestris* VKPM B-4102 (patent RU 1549227, Int. class C12 N 9/00, 1984).

The complex of bacteriolytic enzymes from culture liquid of the bacterium *Xanthomonas campestris* is a basis of 2 drugs: the drug used in medicine was named lysoamidase and the drug used in veterinary—lysomast.

The drug consists of three bacteriolytic enzymes: muramidase, muramoylalanineamidase, endopeptidase, high-polymer polysaccharide, protease, and ballast components (O. A. Stepnaya, L. A. Ledova, I. S. Kulaev, Bacteriolytic enzymes, in: "Uspekhi biologicheskoy khimii", v. XXXIX, Department of scientific and technical information, Pushchino Research Center of Russian Academy of Sciences, Pushchino, 1999, p. 341–346).

The ratio of components in the complex, determined by the authors, is (mas. %):

Bacteriolytic enzymes (muramidase, muramoylalanineamidase, endopeptidase)—1.0–2.0,
Protease—0.5–1.0,
Ballast components—4.0–8.0,
Polysaccharide—the rest.

The three bacteriolytic enzymes possess different substrate specificities to cell wall peptidoglycans of microorganisms: (a) muramidase is an analog of lyzozyme in specificity, (b) muramoylalanineamidase cleaves the peptide portion of peptidoglycan from the polysaccharide one, and (c) endopeptidase destroys the bonds within peptide bridges of the cell wall. Due to the above, the drug actively lyzes cells of a wide range of gram-positive microorganisms, including pathogenic streptococci and staphylococci.

Due to the presence of protease and two of the bacteriolytic enzymes of lysoamidase—endopeptidase and muramoylalanineamidase that possess also proteolytic activity, the drug is good for cleaning wounds from necrotic masses.

The polysaccharide constituent of the complex provides stability of the bacteriolytic enzymes (O. A. Stepnaya, L. A. Ledova, I. S. Kulaev, *Biochemistry* [in Russian], v. 58, 10, 1993, p. 1523–1528). The polysaccharide structure is formed by a repeating unit, consisting of N-acetylglucosamine, N-acetylmannuric and N-acetylgalacturonic acids (L. M. Likhosherstov, S. N. Senchenkova, Y. A. Knirel, et al. FEBS Letters, N 368, 1995, p. 113–116).

The disadvantage of this complex is that its bacteriolytic activity is not high enough due to the presence of ballast components and because nearly the half of the bacteriolytic enzymes are denatured. Besides, the ballast components have no medicinal effect but may cause allergic reactions.

The method of production of a complex of lytic enzymes is known (patent RU 1774658, Int. class C12N 9/36, 1990), which includes cultivation of the strain-producer *Xanthomonas campestris* VKPM B-4102 in a fluid nutrient medium containing glucose, bactopeptone, protein-vitamin concentrate (PVC) in the amount of 2.5–6.0 g/l, and mineral salts, under aeration and stirring, followed by isolation of the target product, with some part of PVC being added to the initial medium. The content of bacteriolytic enzymes in the culture liquid is 40–60 U/ml in bacteriolytic activity units.

Isolation is realized by the method of isolation of the lytic enzyme complex described in the patent RU 1755581 (Int. class C12 N 9/36, 1990), which includes the cooling of culture liquid filtrate, precipitation of the target product by an organic solvent, cooling and separation of precipitate, dialysis and lyophilization. Before precipitation, the filtrate is cooled, acidified to pH 3.5–5.0 followed by addition of 2.5–3.5 v of cooled ethanol, and held in cold place without stirring.

The content of bacteriolytic enzymes in the preparation is no more than 50 U/mg preparation in bacteriolytic activity units.

The yield of finished product is 40–60% of the content of the lytic complex in culture liquid.

Both the content of bacteriolytic enzymes in culture liquid and the yield of finished preparation are not high enough at realization of this method.

The closest to the method proposed, as regards the totality of significant attributes and the effect achieved, is the method of production of a lytic enzyme complex (patent RU 1549227, Int. class C12 N 9/00, 1984) that provides for cultivation of the bacterium *Xanthomonas campestris* VKPM B-4102 on a nutrient medium with the following components (g/l):

| Glucose | 2.0–12.0 |
|---|---|
| Bactopeptone | 2.0–6.0 |

-continued

| | |
|---|---|
| Protein-vitamin concentrate | 2.5–6.0 |
| $Na_2HPO_4 \times 12H_2O$ | 0.5–4.0 |
| $KH_2PO_4$ | 0.1–1.0 |
| NaCl | 0.35–1.0 |
| $MgSO_4 \times 7H_2O$ | 0.2–3.0 |
| $FeSO_4 \times 7H_2O$ | 0.01–0.1 |
| Water | up to 11 |

The process is stopped when a stable lytic activity of culture liquid is reached. Then the biomass is separated by centrifugation, the complex of the lytic enzymes present in the solution is isolated by precipitation with ammonium sulfate, the precipitate is dissolved, and the solution is dialyzed and lyophilized.

The content of bacteriolytic enzymes in culture liquid is no more than 63 U/ml in bacteriolytic activity units.

The yield of end product is not high enough—about 20% of the lytic complex content in culture liquid.

The above method has a disadvantage that the protein-vitamin concentrate is currently not produced by domestic industry, because its production is ecologically unsafe; the use of expensive imported bactopeptone Difco (USA) as a medium component is unpractical, because it significantly increases the cost of the final product.

Besides, the use of ethanol (RU 1755581) and acetone (RU 1549227) for precipitation of the enzymes from culture liquid of the producer results in irreversible denaturing of about the half of bacteriolytic enzymes determining the therapeutic effect of the drug, which are present in the culture liquid (according to the results of bacteriolytic activity measurement and electrophoretic analysis) and, consequently, in a considerable decrease in the product yield (FIG. 1).

Finished lysoamidase preparations produced by the known methods contain a significant amount of minor components—ballast proteins (FIG. 1), which have no medicinal effect but may cause an allergic reaction.

The strain-producer of the complex is known: bacterium *Xanthomonas campestris* VKPM B-4102.

The disadvantage of this strain-producer is that, due to the presence of minor components in the produced complex, bacteriolytic activity is insufficiently high.

BRIEF DESCRIPTION OF THE DRAWING

FIG. 1 shows the protein spectra of bacteriolytic complexes (electrophoresis in polyacrylamide gel) obtained by the known and proposed methods.
 I. Bacteriolytic complex produced by the method described in patent RU 1549227.
 II. Bacteriolytic complex produced by the method described in patent RU 1755581.
 III. Bacteriolytic complex produced by the method proposed.
 IV. Denatured (inactive) portion of enzymes of the complexes produced by the methods of RU 1549227 and RU 1755581.
 V. Preparation of bacteriolytic amidase.
 VI. Preparation of bacteriolytic muramidase.
 VII. Preparation of bacteriolytic endopeptidase.
 VIII. Preparation of bacteriolytic enzyme with the molecular mass 22±0.5 kDa.
 $L_1$-bacteriolytic amidase
 $L_2$-bacteriolytic muramidase
 $L_3$-bacteriolytic endopeptidase
 $L_4$-baeteriolytic enzyme with the molecular mass 20±0.5 kDa.

DISCLOSURE OF INVENTION

The task which should be performed in the inventions applied is to develop a complex of bacteriolytic enzymes.

The technical result expected to obtain if the invention is realized, is an increase of the quantity and the content of bacteriolytic enzymes in culture liquid of the bacterium-producer, an increase of product yield, optimization of the composition of end product (reduction of the content of inactive proteins in the end product), acceleration of production process of finished product.

In this context, the price of the product drops and product production process accelerates.

The essence of the proposed bacteriolytic complex is that it is produced by the strain of the bacterium *Lysobacter* sp. XL1 and, in addition to bacteriolytic enzymes as muramidase, muramoilalanineamidase, endopeptidase, polysaccharide and protease, contains a bacteriolytic enzyme with a molecular weight of about 22 kDa.

The complex contains the components in the following proportion, weight %:

| | |
|---|---|
| Bacteriolytic enzymes (muramidase, muramoilalanineamidase, endopeptidase, bacteriolytic enzyme with molecular weight of about 22 kDa) | 2–5 |
| protease | 1–2 |
| inactive components | 2–4 |
| polysaccharide | the rest |

The proposed preparation—the complex of bacteriolytic enzymes destroys cells of gram-positive microorganisms, including pathogenic ones widely resistant to antibiotics (table 1).

The presence of the additional bacteriolytic enzyme in the preparation increases the bacteriolytic activity of the latter, the complex proposed contains approximately twofold less inactive components, which is demonstrated by the results of electrophoretic analysis presented in FIG. 1. bacteriolytic activity of the complex is 60–90 le/mg.

The essence of the proposed method of production of the bacteriolytic complex is that the strain-producer *Lysobacter* sp. XL1 is cultivated on a nutrient medium with glucose, peptone, yeast extract or yeast autolysate, sodium and potassium phosphates, magnesium sulfate, potassium chloride, iron sulfate and water in the following proportion (g/L):

| | |
|---|---|
| glucose | –2.0–6.0 |
| peptone | –1.5–6.0 |
| yeast extract | –1.0–6.0 |
| or yeast autolysate with amino nitrogen of 440–490 mg/L | –40–300 ml |
| $Na_2HPO_4.12H_2O$ | –4.0–5.0 |
| $KH_2PO_4$ | –1.0–2.0 |
| $MgSO_4.7H_2O$ | –4.0–6.0 |
| KCl | –0.4–1.60 |
| $FeSO_4.7H_2O$ | –0.05–0.20 |
| water | up to 11 |

The process is terminated when the lytic activity of culture liquid is stable, biomass is harvested by centrifugation, the enzyme complex from culture liquid is precipitated by ammonium sulfate (70–85% saturation), the sediment is dissolved, and the solution is dialyzed and freeze-dried.

The technical effect of using the proposed method is achieved by cultivating the strain of the bacterium *Lysobacter* sp. XL1 on a nutrient medium containing glucose, peptone, yeast extract or yeast autolysate, sodium and potassium phosphates, magnesium sulfate, potassium chloride, iron sulfate and water in the following proportion (g/L):

| | |
|---|---|
| glucose | –2.0–6.0 |
| peptone | –1.5–6.0 |
| yeast extract | –1.0–6.0 |
| or yeast autolysate with amino nitrogen of 440–490 mg/L | –40–300 ml |
| Na$_2$HPO$_4$.12H$_2$O | –4.0–5.0 |
| KH$_2$PO$_4$ | –1.0–2.0 |
| MgSO$_4$.7H$_2$O | –4.0–6.0 |
| KCl | –0.4–1.60 |
| FeSO$_4$.7H$_2$O | –0.05–0.20 |
| water | up to 11 | and the complex is precipitated by ammonium sulfate directly from culture liquid.

With the proposed components of the nutrient medium and their proportion, the price of the medium is lower and the content of bacteriolytic enzymes in culture liquid of the producer is raised from 30–60 LE/ml (with the known methods) to 70–90 LE/ml, and the content of inactive proteins in culture medium decreases (FIG. 1).

Bacteriolytic activity during cultivation and in the course of precipitation of the enzyme complex is determined as follows: 0.1 ml of a sample is added to 2 ml of suspension of freeze-dried cells of *Staphylococcus aureus* 209P in 0.01 M Tris-HCl buffer, pH 8.4–8.5, with concentration of 0.5–0.6 units of optical density, warmed up for 10 min at 37° C., and the mixture is incubated for 5 min at 37° C.

The activity is calculated using the following equation $$E \text{ (units/ml)} = \frac{(Do - D) \times P}{t \times 0.01 \times 0.1}$$

where D is optical density of a sample after incubation;
D$_o$ is optical density of the control;
t is time of incubation, minutes;
P is dilution of a sample;
0.01 is optical density corresponding to one unit of the activity;
0.1 is the body of a sample, milliliter (RU patent 1549227).

The increase of magnesium sulfate in the nutrient medium stimulates production of bacteriolytic enzymes.

A change of the procedure of precipitation, namely the exclusion of fractional precipitation by acetone (ru patent 1549227) or by alcohol (ru patent 1755581) from the procedure of purification, reduces duration of the process of the end product obtaining and increases the yield of the target product from 20–50% (with the known methods) to 80–100% of the content in culture liquid.

The strain of the bacterium *Lysobacter* sp. XL1, the producer of bacteriolytic complex, is proposed for use in the method proposed.

The strain of the bacterium *Lysobacter* sp. XL1 (previous *Xanthomonas campestris* XL1) was deposited on Nov. 28, 2000 in All-Russian collection of microorganisms (Pushchino, Moscow region, Prospect Nauki 5 Russian Federation) and designated as VKM B-2249D (Confirmation note on change in name of deposited culture VKM B-2249D, VKM, 14 March 2002).

The strain is obtained by selection on selective media from the strain of the bacterium *Xanthomonas campestris* VKPM B-4102.

Culture-morphological characteristics of the strain

Immobile (no flagella) straight rods, 0.6–0.7×2.0 μm, single or in pairs.

On standard nutrient media (MPA, BBL, Becton Dickinson) the strain forms round colonies of 2 and more μm in diameter, convex, smooth, glistening, slimy, with straight yellow edges, and opaque. Excretes black and brown pigment into the nutrient medium; the time of its appearance and intensity depends on medium composition. Has a mucoid growth on agared medium with 5% glucose. Gram staining by the method of Gregersen (1978) is gram-negative.

Biochemical characteristics

Anaerobe, chemo-organotroph, needs growth factors.
Oxidase- and catalase-positive.
Optimal growth temperature is +25–30° C., grows also at +4° C. and weakly at +15–37° C.
Is not capable of denitrification. Forms acid from glucose under aerobic conditions.
Hydrolyzes gelatin, esculin, and casein.
Forms H$_2$S from peptone.
Grows on media containing up to 4% NaCl.

Identification on the basis of Bergay's Manual of Systematic Bacteriology (Eds. Noel R. Krieg, John G. Holt, Baltimore; London Williams & Wilkins. 1984, v. 1) refers this bacterium to the species *Xanthomonas campestries* or the genus *Lysobacter*.

Selected strain does not form urease, does not hydrolyze starch, peptonizes milk, dilutes gelatin, destroys chitin, produces processes and lytic enzymes, and has 68 mol % GC base pairs.

Both initial and selected bacteria have significant differences from the bacteria of the genus *Xanthomonas*, to which they had been attributed previously.

The initial bacterium (the bacterium from which the proposed strain was selected), was isolated from river water but not from plants and is not an agent of vascular bacteriosis of plants, immobile, secretes lytic enzymes, proceases, and chitinases. These facts also evidence that the above bacterium belongs to the genus *Lysobacter*. This conclusion is made on the basis of materials of the paper on formation of the new genus *Lysobacter* (Christensen, P., Cook, F.D.: *Lysobacter*, a new genus of nonfruiting, gliding bacteria with a high base ratio. Int. J. Syst. Bacteriol. 28: 367–393 (1978)), as well as Bergey's manual of systematic bacteriology. Eds., James T. Staley, Marvin P. Bryant, Norbert Pfenning, John G. Holt. Baltimore; London. Williams & Wilkins. 1984, v.3, p. 2083–2086.

The nucleotide sequence of the gene coding 16-S RNA has been determined. The sequence was analyzed using computer programs of DNA and RNA analysis, available in the database "Ribosomal Database Project" (http://rdp.c-me.msu.edu/html/). The information about this database is published in: Maidak B. L., Cole J. R., Lilburn T. G., Parker C. T. Jr, Saxman P. R., Farris R. J., Garrity G. M., Olsen G. J., Schmidt T. M., Tiedje J. M. The RDP-II (Ribosomal Database Project). Nucleic Acids Res. 2001 Jan. 1; 29(1): 173–4.

Based on the sequence analysis, the above bacteruim must be attributed to the genus *Lysobacter*, phylogenetic group *Xanthomonas-Lysobacter*.

The above characteristics, together with the characteristics determined previously at deposition of the strain under study also make if possible to refer it to the genus *Lysobacter*.

However, the available data do not allow an unambiguous attribution of the strain to any of the species of the genus *Lysobacter*.

By the totality of characteristics available, the culture was referred to the species *Lysobacter* sp.

The strain *Lysobacter* sp. XL1 is not pathogenic for man and animals. The strain produces a bacteriolytic complex including bacteriolytic enzymes (muramidase, muramoylalanineamidase, endopeptidase, bacteriolytic enzyme with the molecular mass of about 22 kDa), protease, acid high-molecular polysaccharide, and ballast components.

FIG. 1 shows the protein spectra of bacteriolytic complexes (electrophoresis in polyacrylamide gel) obtained by the known and proposed methods.

The possibility of realization of the method is supported by, but not limited to, the following examples.

EXAMPLE 1

Flask 750 ml is filled with 150 ml of a nutrient medium with the following composition (g/l):

| | |
|---|---|
| Glucose | 5.0 |
| Peptone | 2.0 |
| Yeast extract | 2.5 |
| $Na_2HPO_4 \times 12H_2O$ | 4.0 |
| $KH_2PO_4$ | 1.0 |
| KCl | 0.5 |
| $MgSO_4 \times 7H_2O$ | 3.0 |
| $FeSO_4 \times 7H_2O$ | 0.1 |
| Water | up to 1 liter, | pH of the medium is brought to 7.0 by 10% NaOH solution. The flask with the medium is sterilized. 10% of inoculum of the bacterium *Lysobacter* sp. XL1 is introduced into the sterile flask with the medium and cultivated for 24 h at 29° C. on a shaker (200 rpm). Bacterial cells are separated by centrifugation.

By hour 24 of cultivation, the bacteriolytic activity of culture liquid is 72 LU/ml.

EXAMPLE 2

The strain *Lysobacter* sp. XL1 is cultivated as described in Example 1 on a medium of the following composition, g/l:

| | |
|---|---|
| Glucose | 5.0 |
| Peptone | 2.0 |
| Yeast autolysate | 100 ml |
| $Na_2HPO_4 \times 12H_2O$ | 4.2 |
| $KH_2PO_4$ | 1.0 |
| KCl | 0.6 |
| $MgSO_4 \times 7H_2O$ | 5.0 |
| $FeSO_4 \times 7H_2O$ | 0.1 |
| Water | up to 1 liter. |

By hour 24 of cultivation, the bacteriolytic activity of culture liquid is 70 LU/ml.

EXAMPLE 3

The strain-producer is cultivated as described in Example 1 on a medium of the following composition, g/l:

| | |
|---|---|
| Glucose | 5.0 |
| Peptone | 2.0 |
| Yeast extract | 2.0 |
| $Na_2HPO_4 \times 12H_2O$ | 4.2 |
| $KH_2PO_4$ | 1.0 |
| KCl | 0.6 |
| $MgSO_4 \times 7H_2O$ | 5.0 |
| $FeSO_4 \times 7H_2O$ | 0.1 |
| Water | up to 1 liter. |

By hour 24 of cultivation, the bacteriolytic activity of culture liquid is 90 LU/ml.

EXAMPLE 4

Ankum fermenter is filled with 6 liters of a medium of the following composition (g/l):

| | |
|---|---|
| Glucose | 5.0 |
| Peptone | 2.0 |
| Yeast extract | 2.0 |
| $Na_2HPO_4 \times 12H_2O$ | 4.2 |
| $KH_2PO_4$ | 1.0 |
| KCl | 0.6 |
| $MgSO_4 \times 7H_2O$ | 5.0 |
| $FeSO_4 \times 7H_2O$ | 0.1 |
| Water | up to 1 liter. |

Sterilized at 0.5 kg-f/cm$^2$ for 30 min.

300 ml of inoculum grown on the above medium is introduced into the fermenter under sterile conditions. Cultivation is run at 29° C., air feeding of 0.3 v per 1 v of the medium per 1 min, so that the partial pressure of oxygen in the medium would not fall below 30% of saturation.

The pH of the medium is maintained in the range of 6.3–7.5, with 10% NaOH solution or 10% HCl solution fed to the medium when pH decreases or increases, respectively. By hour 24 of cultivation, the activity of culture liquid is 70 LU/ml.

Cooled culture liquid (5.6 l) is supplemented with ammonium sulfate to 80% saturation, left over for 12 h, and precipitate is separated by centrifugation. The precipitate is dissolved in water, dialyzed, the dialysis yielding 500 ml of a solution containing the bacteriolytic complex.

The solution is lyophilized to obtain about 5 g of the preparation with the activity 72 LU/ml of preparation.

Total bacteriolytic activity of culture liquid is 355320 LU; total activity of end product is 360000 LU. The yield of finished product is 100% of the content in culture liquid.

Results of electrophoretic analysis of lysoamidase preparations obtained by the known methods and by the method proposed are presented in FIG. 1.

EXAMPLE 5

The culture-producer *Lysobacter* sp. XL1 is grown in an Ankum fermenter as in Example 4 on the medium described in Example 2. By hour 24, the activity of culture liquid is 65 LU/ml. When the end product is obtained by the scheme given in Example 4, the bacteriolytic activity of the preparation is 60 LU/mg. The yield of end product is 100%.

Electrophoretic analysis of end products showed that when the complex is obtained by the known methods, the end product has a great quantity of ballast proteins, many of them occurring in the preparation in the same amounts as bacteriolytic enzymes.

The end product obtained by the method proposed contains much less ballast proteins and is enriched in bacteriolytic enzymes.

The data from Table 1 show that the proposed preparation, as compared with the known one, lyzes additionally 10 bacterial strains of seven species and lyzes additionally cells of 18 clinical strains of *Staphylococcus aureus* isolated directly from patients.

Thus, the proposed method increases the content of bacteriolytic enzymes in the culture liquid of the producer—*Lysobacter* sp. XL1, increases the yield of end product, decreases the content of ballast proteins in the end product (FIG. 1).

Besides, the method reduces the time of production of end product and the cost of end product.

INDUSTRIAL APPLICABILITY

The bacteriolytic complex may be used in medicine for treating infectious diseases caused by pathogenic antibiotic-resistant microorganisms, in particular, in surgery, gynecology, stomatology, otolaryngology, cosmetology, as well as in veterinary to treat *staphylococcosis* in poultry and mastitis in cattle.

Besides, the bacteriolytic complex may be used in research practice to obtain cell culture, to obtain protoplasts, to isolate cell contents for gene engineering, to study the cell wall structure of microorganisms. The proposed strain-producer of the bacteriolytic complex and the method of its production may be used in biotechnology to produce the complex preparation.

TABLE 1

Microbial range of action of bacteriolytic complexes

| Preparation by patent | Proposed preparation |
| --- | --- |
| Gram-positive microorganisms | Gram-positive microorgniams |
| *Staphylococcus aureus* 61 strain | *Staphylococcus aureus* 79 strains |
| *S. epidermidis* 3 strains | *S. epidermidis* 3 strains |
| *S. saprofiticus* 1 strain | *S. saprofiticus* 1 strain |
| *Streptococcus viridans* 2 strains | *Streptococcus viridans* 2 strains |
| *S. pyogenes* 2 strains | *S. pyogenes* 2 strains |
| *S. agalactiae* 3 strains | *S. agalactiae* 3 strains |
|  | *S. mutans* 2 strains |
|  | *Peptostreptococcus intermedius* 1 strain |
| *Corynebacterium xerosis* 1 strains | *Corynebacterium flavum* 1 strain |
|  | *Streptomyces azureus* 1 strain |
|  | *S. chrysomallus* 1 strain |
|  | *Bacillus subtilis* 2 strains |
|  | *Arthrobacter globiformis* 1 strain |
|  | Gram-negative microorganisms |
|  | *Fusobacterium necroforum* 1 strain |
|  | *Prevotella melaninogenica* 1 strain |

The invention claimed is:

1. An isolated bacteriolytic complex produced by the strain of the bacterium *Lysobacter* sp. XL1, having been deposited in All-Russian collection of microorganisms under accession number VKM B-2249 D, wherein the isolated bacteriolytic complex includes muramidase, muramoylalanineamidase, endopeptidase, protease, a polysaccharide and a bacteriolytic enzyme, wherein the bacteriolytic enzyme has a molecular mass of about 22 kDa.

2. A method of production of a bacteriolytic complex, said complex including muramidase, muramoylalanineamidase, endopeptidase, protease, a polysaccharide and a bacteriolytic enzyme, wherein the bacteriolytic enzyme has a molecular mass of about 22 kDa, said method comprising the steps of:

a) cultivation of the strain of bacterium *Lysobacter* sp. XL1 having been deposited in All-Russian collection of microorganisms under accession number VKM B-2249 D, on a nutrient medium comprising glucose, peptone, yeast extract or yeast autolysate, phosphate salts of sodium and potassium, magnesium sulfate, potassium chloride, iron sulfate and water, wherein the amounts (g/l) are:

| | |
| --- | --- |
| Glucose | 2.0–6.0 |
| Peptone | 1.5–6.0 |
| Yeast extract | 1.0–6.0 |
| or yeast autolysate with amine nitrogen 440–490 mg/l | 40–300 ml |
| $Na_2HPO_4 \times 12H_2O$ | 4.0–5.0 |
| $KH_2PO_4$ | 1.0–2.0 |
| $MgSO_4 \times 7H_2O$ | 4.0–6.0 |
| KCl | 0.4–1.60 |
| $FeSO_4 \times 7H_2O$ | 0.05–0.20 |
| Water | up to 1 liter., | b) separating of a biomass containing the complex from a culture liquid by centrifugation;

c) precipitating the complex by ammonium sulfate;

d) dissolving the complex;

e) dialysing the dissolved complex and f) lyophilizing of the resulting complex.

3. A biologically pure culture of the strain *Lysobacter* sp. XL1 having been deposited in the All-Russian collection of microorganisms under accession number VKM B-2249 D.

4. The strain according to claim 3 that produces a bacteriolytic complex including muramidase, muramoylalanineamidase, endopeptidase, protease, a polysaccharide and a bacteriolytic enzyme, wherein the bacteriolytic enzyme has a molecular mass of about 22 kDa.

* * * * *